ABSTRACT

The administration to mammals of prostaglandin $PGA_2$, derivatives of $PGA_2$, methyl ester of ω-homo $PGE_1$ and compounds structurally related to prostaglandins, such as alkyl 11,15-dihydroxy-15-alkyl-9-oxoprost-13-ynates and 11-methyl-15-hydroxy-9-oxoprosta-5-cis-13-trans-dienoic acid results in a state of tranquilization as opposed to general depression.

4 Claims, No Drawings

---

United States Patent [19] — Potts

[11] 3,931,411
[45] Jan. 6, 1976

[54] METHOD FOR TRANQUILIZATION WITHOUT GENERAL DEPRESSION
[75] Inventor: Walter Joseph Potts, Glenview, Ill.
[73] Assignee: G. D. Searle & Co., Chicago, Ill.
[22] Filed: Dec. 26, 1973
[21] Appl. No.: 428,077

Related U.S. Application Data
[63] Continuation-in-part of Ser. No. 151,564, June 9, 1971, Pat. No. 3,792,179.

[52] U.S. Cl. .............................. 424/312; 424/318
[51] Int. Cl.² ................. A61K 31/20; A61K 31/23
[58] Field of Search ............................ 424/312, 318

[56] References Cited
OTHER PUBLICATIONS
Ellis et al., – Progress in Medicinal Chemistry, Vol. 8, (1971), pp. 363 & 364.

Primary Examiner—Stanley J. Friedman
Attorney, Agent, or Firm—Elliot N. Schubert; John J. McDonnell

METHOD FOR TRANQUILIZATION WITHOUT GENERAL DEPRESSION

This application is a continuation-in-part of my co-pending application Ser. No. 151,564, filed June 9, 1971, now U.S. Pat. No. 3,792,179.

The present invention is concerned with methods of utilizing prostaglandins or prostaglandin-like compounds in mammals to induce tranquility without general depression. In addition, these compounds are advantageously short acting. Compounds of the following general formulae are suitable for practicing the present invention

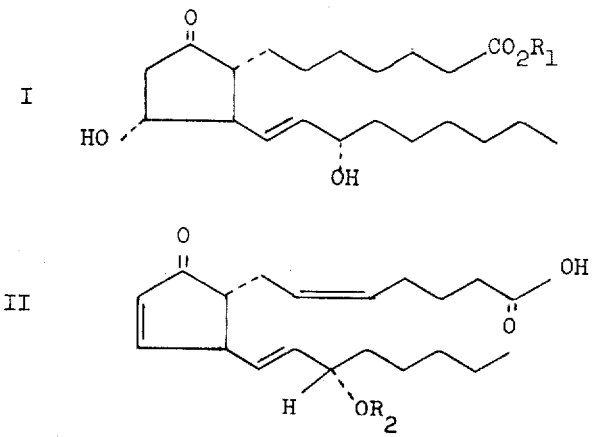

wherein $R_1$, $R_3$ and $R_4$ is each a lower alkyl radical containing 1–6 carbon atoms and $R_2$ is hydrogen or alkanoyl having 1–6 carbon atoms. $R_5$ is hydrogen or lower alkyl.

Thus compounds of the formula

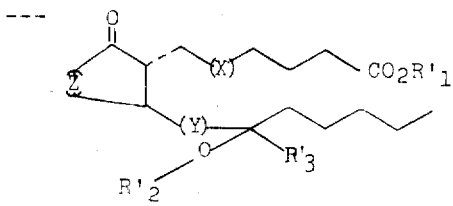

wherein $R'_1$ and $R'_3$ represent hydrogen or lower alkyl containing 1–7 carbon atoms, $R'_2$ represents hydrogen or acyl, X represents ethylene or cis vinylene, Y represents trans vinylene or ethynylene, and Z represents cis vinylene, or hydroxy-/or (lower alkyl)-substituted ethylene in which the methylene portion is adjacent to the carbonyl of the cyclopentane ring in the formula are suitable for practicing this invention.

Compounds particularly suitable for practicing the present invention are 15(S)-hydroxy-9-oxo-5-cis-10,13-trans-prostatrienoic acid (PGA$_2$), 15(S)-acetoxy-9-oxo-5-cis-10,13-trans-prostatrienoic acid, prepared by treating PGA$_2$ with acetic anhydride in pyridine, methyl 15(S)-11β,15-dihydroxy-20-methyl-9-oxoprost-13-trans-enoate (British Patent No. 1,269,656), 3(RS)2-(3-hydroxy-1-heptynyl)-5-oxocyclopent-1-eneheptanoic acid, 2-(3-hydroxy-1-octynyl)-5-oxocyclopent-1-eneoctanoic acid, methyl 3(R)-hydroxy-2α-(3(S)-hydroxy-3(R)-methyl-1-octynyl)-5-oxocyclopentane-1β-heptanoate, 2-((3RS)3-hydroxy-1-nonynyl)-3-hydroxy-5-oxocyclopent-1-eneheptanoic acid, and 15(S)-hydroxy-11-methyl-9-oxoprosta-5-cis-13-trans-dienoic acid.

Also suitable for the purposes of this invention are the pharmaceutically acceptable salts of the aforementioned compounds as illustrated by the salts of alkali and alkaline earth metals such as lithium, sodium, potassium, calcium, and magnesium and salts of ammonia or a primary, secondary or tertiary basic amine such as mono-, di-, or triethylamine, benzylamine, a heterocyclic amine such as piperidine or morpholine, or an amine containing one or more water-solublizing or hydrophilic groups such as triethanolamine and phenylmonoethanolamine.

The compounds of this invention may be administered parenterally by injections, intravenous solutions, and the like or by alimentary canal in the form of oral dosages or by suppository. Doses of 0.56 to 9.0 mg./kg. are effective amounts for practicing this invention. Combinations of compounds of this invention with pharmaceutical carriers and adjuvants will be recognized by those skilled in the pharmaceutical arts.

The following examples describe in detail various applications of the means of this invention and their implementation. However, the invention is not to be construed as limited thereby, either in spirit or in scope, since it will be apparent to those skilled in the art that many modifications both of techniques and of materials, may be practiced without departing from the purpose and intent of this disclosure.

EXAMPLE 1

To a solution of 56.5 parts of potassium metal in 936 parts of tertiary-butyl alcohol is added successively 102 parts of dimethyl oxalate and a solution of 54 parts of 9-oxodecanoic acid in 156 parts of tertiarybutyl alcohol. That addition is carried out over a period of about 40 minutes while the mixture is heated at the reflux temperature in an atmosphere of nitrogen. At the end of the addition period, heating is continued for about 90 minutes longer and the reaction mixture is cooled and filtered under nitrogen. The filter cake is added to a solution of dilute hydrochloric acid and that mixture is extracted with chloroform. The chloroform layer is separated, washed with water, dried over anhydrous sodium sulfate and stripped of solvent under reduced pressure. Recrystallization of the resulting residue from ether affords 2,3,5-trioxo-4-methoxalylcyclopentaneheptanoic acid, melting at about 127°–129°.

A mixture containg 50 parts of 2,3,5-trioxo-4-methoxalylcyclopentaneheptanoic acid and 2,880 parts by volume of 2N hydrochloric acid is slowly distilled in a nitrogen atmosphere for about 2 hours, then is cooled and decolorized with activated carbon. The filtrate thus obtained is concentrated to dryness under reduced pressure and the resulting residue is extracted with ethyl acetate. That organic solution is washed several times with saturated aqueous sodium chloride, then with water and finally dried over anhydrous sodium sulfate and stripped of solvent by distillation under reduced pressure. Recrystallization of the resulting residue from water affords pure 2,3,5-trioxocyclopentaneheptanoic acid, melting at about 102°–104°.

A mixture containing 45.7 parts of 2,3,5-trioxocyclopentaneheptanoic acid, 13 parts of 5% palladium-on-carbon catalyst, 453 parts of glacial acetic acid and 63.3 parts of concentrated sulfuric acid is shaken with hydrogen at a pressure of 3 atmospheres until 2 molecular equivalents of hydrogen are absorbed. The reaction mixture is then filtered and the resulting filtrate is mixed with 100 parts of solid sodium acetate. Evaporation of the mixture to dryness affords a solid residue which is extracted with water. The resulting extract is filtered and the filter cake is washed with water, dried, then recrystallized from acetone to afford white crystals of 2,5-dioxocyclopentaneheptanoic acid, melting at about 160°–161.5°.

A mixture containing 26 parts of 2,5-dioxocyclopentaneheptanoic acid, 560 parts of ethanol, 440 parts of benzene and 14.7 parts of concentrated sulfuric acid is slowly distilled over a period of about 40 hours, during which time approximately 200 parts of distillate is collected. The residual mixture is cooled, diluted with approximately 350 parts of ether, then washed successively with dilute aqueous sodium hydroxide and water. The resulting neutral solution is dried over anhydrous sodium sulfate and evaporated by dryness under reduced pressure to afford, as a yellow liquid, ethyl 2-ethoxy-5-oxocyclopent-1-eneheptanoate, which substance is characterized by an ultraviolet absorption maximum at about 253.5 millimicrons.

A mixture containing 22.16 parts of ethyl 2-ethoxy-5-oxocyclopent 1-eneheptanoate, 785 parts of 0.1N aqueous sodium hydroxide and 320 parts of ethanol is stored at room temperature for about 48 hours, then is concentrated to approximately ⅔ volume by distillation under reduced pressure. The residual solution is washed with ether, acidified with dilute hydrochloric acid, then extracted with ethyl acetate. The ethyl acetate extracts are washed with water, dried over anhydrous magnesium sulfate and evaporated to dryness by distillation under reduced pressure. The residual solid residue is purified by recrystallization from ether-benzene to afford 2-ethoxy-5-oxocyclopent-1-eneheptanoic acid, melting at about 65°–66°.

To a solution of 0.3 part of (3RS) 1-heptyn-3-ol in 53 parts of benzene is added 29.7 parts of dihydropyran and 0.15 part of p-toluenesulfonic acid. The initial exothermic reaction is controlled by cooling in an ice bath and the temperature is thus maintained at about 23°. The resulting reaction mixture is allowed to stand at room temperature for about 5 hours, then is diluted with benzene, washed successively with dilute aqueous sodium hydroxide and water, dried over anhydrous sodium sulfate and stripped of solvent under reduced pressure to afford, as a colorless liquid, 3(RS) 1-heptyn-3-ol 3-tetrahydropyran-2'-yl ether. It is characterized by infrared absorption maxima, in chloroform, at about 3.01, 3.38, 3.48, 6.58, 6.63, 6.80, 8.90, 9.30, 9.63, 9.80, and 10.21 microns.

To a solution of 12.6 parts of (3RS) 1-octyn-3-ol 3-tetrahydropyran-2'-yl ether in 112 parts of tetrahydrofuran is added 15.25 parts by volume of 3.3 M ethereal ethyl magnesium bromide and the resulting reaction mixture is allowed to stand at room temperature for about 2 hours. This solution containing (3RS) 3-tetrahydropyran-2'-yloxy-1-heptynyl magnesium bromide is used as such in the following procedure.

To 15.7 parts of the Grignard reagent prepared above, dissolved in 112 parts of tetrahydrofuran, is added 2.54 parts of 2-ethoxy-5-oxocyclopent-1-eneheptanoic acid dissolved in 67.5 parts of tetrahydrofuran. The reaction mixture is kept under an atmosphere of nitrogen and is stirred at room temperature for about 24 hours, at the end of which time it is poured into approximately 350 parts of cold water. Acidification of that aqueous mixture with dilute hydrochloric acid is followed by extraction of the resulting acidic mixture with ether. The ether extracts are combined, then extracted several times with dilute aqueous potassium carbonate. Those alkaline extracts are combined, washed with ether and made acidic by the addition of dilute hydrochloric acid. Extraction of the latter mixture with ether affords an organic solution, which is dried over anhydrous sodium sulfate and concentrated to dryness under reduced pressure to afford, as a reddish brown oil displaying an ultraviolet maximum at about 269 millimicrons, (3RS) 2-(3-tetrahydropyran-2'-yloxy-1-heptynyl)-5-oxocyclopent-1-eneheptanoic acid. It is represented by the following structural formula

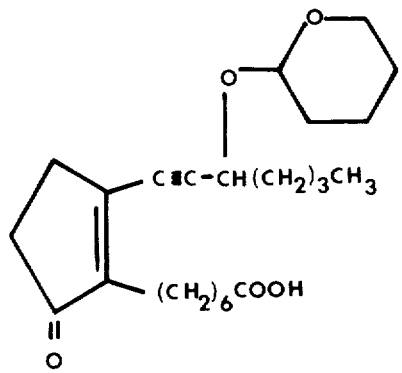

A mixture containing 3.5 parts of (3(RS) 2-(3-tetrahydropyran-2'-yloxy-1-heptynyl)-5-oxocyclopent-1-eneheptanoic acid, 48 parts of acetone, 30 parts of water, 1.6 parts of methanol and 1.2 parts of concentrated hydrochloric acid is allowed to stand at room temperature for about 4 hours. At the end of that reaction period, the mixture is concentrated to approximately ½ volume, then is made alkaline by the addition of dilute aqueous potassium carbonate. The alkaline solution is washed several times with ether, then is acidified with dilute hydrochloric acid and the resulting acidic solution is extracted with ether. The ether extracts are combined, dried over anhydrous sodium sulfate and evaporated to dryness under reduced pressure, thus affording a solid residue, which, after recrystallization from wet ether, affords (3RS) 2-(3-hydroxy-1-heptynyl)-5-oxocyclopent-1-eneheptanoic acid monohydrate, melting at about 41°–43° and displaying an ultraviolet absorption maximum at about 270 millimicrons. Dehydration of that monohydrate by heating under reduced pressure affords (3RS) 2-(3-hydroxy-1-heptynyl)-5-oxocyclopent-1-eneheptanoic acid as a viscous oil. It is represented by the following structural formula

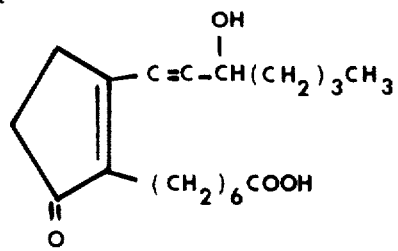

EXAMPLE 2

(3S) 2-(3-hydroxy-1-octynyl)-5-oxocyclopent-1-eneoctanoic acid is prepared as set out in Example 1 except that 9-oxodecanoic acid is replaced with 156 parts of 10-oxoandecanoic acid and 1-heptyn-3-ol is replaced with 0.3 part of (3S)1-octyn-3-ol. The structure of this compound is

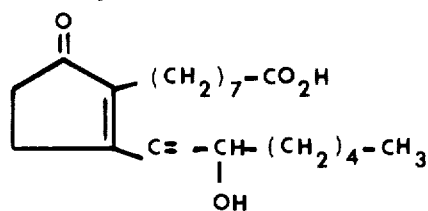

EXAMPLE 3

A solution of 1.47 parts of 3(RS) 3-methyl-3-(tetrahydropyran-2-yl)oxy-1-octyne in 7.1 parts of ether is treated at −50° with 2.6 parts by volume of a 2.3 M butyl lithium in hexane solution. That mixture is stirred at room temperature for 1 hour and then cooled to −40°. 2.47 Parts by volume of a 0.81 M boron trichloride in toluene solution is added and the resulting solution is stirred at −30° − −20° for 30 minutes. After that time, an ethereal solution containing 0.240 part of methyl 3(RS)-hydroxy-5-oxocyclopent-1-eneheptanoate, Rec. Trav. Chim. 87 1421 (1968), is added and the resulting reaction mixture is stirred at −20° for 1 hour, at 0° for 2 hours and at room temperature for 2 hours. The crude reaction product is separated by column chromatography, elution being with 30% ethyl acetate in benzene to provide the compound which is a mixture of racemic methyl 3(R)-hydroxy-2α-(3(R)-hydroxy-3(S)-methyl-1-octynyl)-5-oxocyclopentane-1β-heptanoate and racemic methyl 3(R)-hydroxy-2α-(3(S)-hydroxy-3(R)-methyl-1-octynyl)-5-oxocyclopentane-1β-heptanoate having the structure

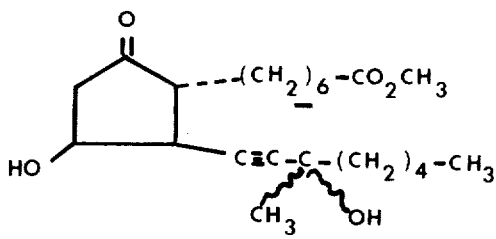

EXAMPLE 4

To a stirred solution of 150 parts of (3RS)1-nonyn-3-ol 3-tetrahydropyran-2'-yl ether in about 1954 parts of dry tetrahydrofuran is added dropwise 283 parts by volume of 3 N ethereal ethyl magnesium bromide while keeping the temperature of the solution below 30°. Stirring is continued for about 1 ½ hours, after which time 31.5 parts of 2-methoxy-4-methoxymethoxy-5-oxocyclopent-1-eneheptanoic acid (U.S. Ser. No. 261,642, allowed Aug. 21, 1973) in about 710 parts of dry tetrahydrofuran is added, over a 10 minute period, to the stirred solution. The reactants are allowed to stand for about 16 hours. Then dilute hydrochloric acid is added and the tetrahydrofuran is distilled, while maintaining the temperature below 40°, to reduce the volume of the solution to about ⅓ of its original volume. Benzene is added, and then the organic layer is separated and washed with water. The solvent is evaporated yielding 5-hydroxy-5-((3RS) 3-tetrahydropyran-2'-yloxy-1-nonynyl)-4-methoxymethoxy-2-methoxycyclopent-1-eneheptanoic acid as an oily residue.

This crude oil is dissolved in 4400 parts of acetone, 1600 parts of water, and 71 parts of concentrated hydrochloric acid and refluxed for 20 hours. The acetone is removed under reduced pressure and then the aqueous solution is extracted with a 1:1 benzene-ether mixture. The benzene-ether solution is extracted with a 5% potassium carbonate solution, and the potassium carbonate solution is acidified and extracted into a benzene-ether solution which is then dried and stripped of solvent. The resulting oil is chromatographed on silicic acid to yield a crystalline material which is triturated with a benzene-ether solution and then recrystallized from ether. The resulting product is 2-((3RS) 3-hydroxy-1-nonylyl)-3-hydroxy-5-oxocyclopent-1-eneheptanoic acid. This compound is represented by the following structural formula

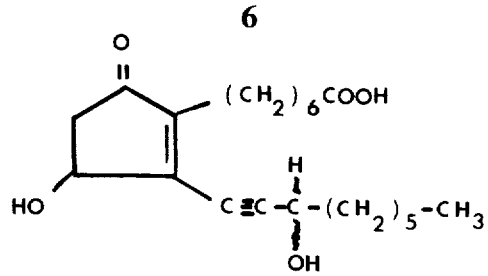

EXAMPLE 5

To a cold stirred suspension consisting of 5.2 parts of cuprous iodide with 200 parts by volume of ether is added, over a period of about 5 minutes at 0°, 18 parts by volume of 3 M ethereal methyl magnesium bromide. While the temperature of that mixture is kept at about 0°, a solution containing 5.5 parts of methyl 15(S)-acetoxy-9-oxoprosta-5-cis-10,13-trans-trienoate (Weinheimer and Spraggins, Tetrahedron Letters, 5185 (1969)) in 100 parts by volume of ether is added dropwise over a period of about 50 minutes. The reaction mixture is stirred at about 0° for an additional 30 minutes, then is poured, with stirring, into a cold solution of 124 parts of ammonium chloride in 415 parts of water. That aqueous mixture is extracted several times with ethyl acetate and the combined organic extracts are washed with water, dried over anhydrous sodium sulfate, then concentrated under reduced pressure to afford the oily product. The material is dissolved in 220 parts of methanol and the resulting solution is diluted with aqueous sodium hydroxide, prepared by dissolution of 1.1 parts of sodium hydroxide in 70 parts of water. That mixture is kept at room temperature for approximately 72 hours, then is partially concentrated and diluted with aqueous citric acid. The product is extracted from that mixture with ethyl acetate and the organic extract is washed with water, dried over anhydrous sodium sulfate, then concentrated to dryness under reduced pressure. The resulting crude product is purified by adsorption on a silicic acid chromatographic column followed by elution with 25% ethyl acetate in benzene. Further purification is effected by recrystallization from ether-pentane, thus affording 15(S)-hydroxy-11-methyl-9-oxoprosta-5-cis-13-trans-dienoic acid, melting at about 64°–66°. The structure of this compound is

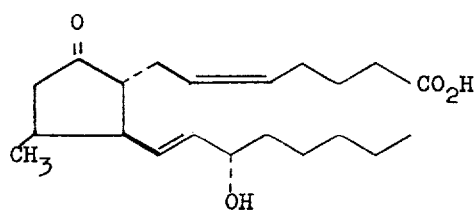

EXAMPLE 6

To each of a group of 12 naive Charles River male rats weighing 200–225 g. is administered intraperitoneally 1.125 mg./kg. body weight of $PGA_2$ in a volume of 1 ml. normal saline/kg. body weight either 5 or 30 minutes before testing. Similar groups of 12 animals are treated in the identical manner except that either normal saline or 2.25 or 4.5 mg./kg. of $PGA_2$ is used. The rats are then placed in Lehigh Valley shuttle cages, are allowed to acclimate for approximately 1 minute, then are subjected initially to a 5 second conditioned stimulus, consisting of a tone and a light, and finally to a 0.2 ma. footshock delivered to the grid floor of the cage. The shock is automatically terminated after 30 seconds if the rat fails to respond. The aminal can either avoid or escape the shock by moving to the other side of the shuttle cage. If the shuttle response occurs during the conditioned stimulus period, the conditioned stimulus is terminated, onset of the shock is prevented and the reaction is scored as an avoidance response. If the shuttle response occurs during the shock period, the shock is terminated and the reaction is scored as an escape response. Each conditioned stimulus presentation is separated by a 15 second interval. If the shuttle response occurs during that inverval, it is scored as an intertrial interval response.

The results of this assay are shown in Table I. The data are analyzed by means of Student's t tests. From that data it is concluded that, in naive rats, the administration of $PGA_2$ 5 minutes prior to test produces a significant reduction in avoidance responses at doses of 2.25 and 4.5 mg./kg. body weight without a significant effect on escape latency.

EXAMPLE 7

The test disclosed in Example 6 is repeated with similar groups of trained rather than naive rats weighing 300–325 g., which rats have been treated with 0.56, 1.12, 2.25, 4.5 or 9.0 mg./kg. of $PGA_2$. In this study each group contains eight animals. The data are analyzed by means of paired Student's $t$ tests. Table II summarizes the mean differences between the control session and the drug session. Positive numbers indicate the drug scores which are higher than control scores, while negative numbers indicate the drug scores which are lower than control. It is seen from those results that the administration of $PGA_2$ 5 minutes prior to test at doses of 4.5 or 9.0 mg./kg. causes a significant decrease in avoidance responses with no loss of escape responses, thus indicating a tranquilizing rather than generalized depressant effect. The separation between tranquilizing and generalized depressant properties is shown again by the pronounced effect of the drug on avoidance latency and longest run of avoidance responses with relatively little effect on escape latency.

EXAMPLE 8

The procedure of Example 6 is repeated using naive rats and 2.25, 4.5 and 9.0 mg./kg. doses of 15(S)-acetoxy-9oxo-5-cis-10,13-trans prostatrienoic acid. The results of the tests carried out 5 minutes after injection are shown in Table III. The results indicate that at all doses there is a significant decrease in avoidance responses while no effect on escape latency is observed.

EXAMPLE 9

The procedure in Example 7 is repeated using trained rats and 0.035, 0.07, 0.14, 0.28, 0.56 and 1.12 mg./kg. doses of methyl 15(S)-11β,15-dihydroxy-20,methyl-9-oxoprost-13-trans enoate. The results with animals injected 5 minutes prior to test are included in Table IV. Those data demonstrate a significant reduction in avoidance responses at all doses tested and a significant decrease in the longest run of avoidance responses at 0.07, 0.28, 0.57 and 1.12 mg./kg. while showing little or no loss of escape response.

EXAMPLE 10

3RS 2-(3-hydroxy-1-heptynyl)-5-oxocyclopent-1-eneheptanoic acid is tested as set out in Example 6 and has a significant reduction in avoidance response at a dose of 9 mg./kg. body weight without a significant effect on escape latency.

EXAMPLE 11

(3S) 2-(3-hydroxy-1-octynyl)-5-oxocyclopent-1-eneoctanoic acid is tested as set out in Example 6 and has a significant reduction in avoidance response at a dose of 9 mg./kg. body weight without a significant effect on escape latency.

EXAMPLE 12

Racemic methyl 3(R)-hydroxy-2α-(3(R)-hydroxy-3(S)-methyl-1-octynyl)-5-oxocyclopentane-1β-heptanoate and racemic methyl 3(R)-hydroxy-2α-(3(S)-hydroxy-3(R)-methyl-1-octynyl)-5-oxocyclopentane-1β-heptanoate is tested as set out in Example 6 and has a significant reduction in avoidance response at a dose of 9 mg./kg. body weight without a significant effect on escape latency.

EXAMPLE 13

2-((3RS) 3-hydroxy-1-nonylyl)-3-hydroxy-5-oxocyclopent-1-eneheptanoic acid is tested as set out in Example 6 and has a significant reduction in avoidance response at a dose of 9 mg./kg. body weight without a significant effect on escape latency.

EXAMPLE 14

15(S)-hydroxy-11-methyl-9-oxoprosta-5-cis-13-trans dienoic acid is tested as set out in Example 6 and has a significant reduction in avoidance response at a dose of 9 mg./kg. body weight without a significant effect on escape latency.

TABLE I

| | Mean values under control and drug conditions for naive rats | | | |
| | | Dose — 5 Minute Post Injection | | |
| Measure | Control | 1.125 mg/kg | 2.25 mg/kg | 4.5 mg/kg |
| --- | --- | --- | --- | --- |
| Total Avoidance Responses | 28.58 | 27.17 | 13.36[a] | 13.18[a] |
| Avoidance Responses Trials 1–50 | 8.00 | 3.42[a] | 1.27[b] | 2.91[a] |
| Avoidance Responses Trials 51–100 | 20.58 | 23.75 | 12.09 | 10.27 |
| Intertrial Interval Responses | 33.42 | 24.92 | 20.55[a] | 31.09 |
| Escape Latency (sec) | .57 | .75 | .57 | 1.52 |

[a]$p \leq .05$ t test, two tailed
[b]$p \leq .01$ t test, two tailed

Table II

Mean difference between control and each dose condition for trained rats. Positive numbers indicate the drug score was higher; negative numbers indicate the drug score was lower than control

| Measure | .56 mg/kg | 1.12 mg/kg | Doses — 5 Minute Post Injection 2.25 mg/kg | 4.5 mg/kg | 9.0 mg/kg |
|---|---|---|---|---|---|
| Total Avoidance Responses | −.75 | −3.12 | −10.25 | −31.75[a] | −77.00[b] |
| Avoidance Responses Trials 1—50 | −1.12 | −2.37 | −9.62[a] | −18.50[a] | −36.12[b] |
| Avoidance Responses Trials 51—100 | +.37 | −.75 | −.62 | −13.25 | −40.87[b] |
| Avoidance Latency (sec) | −.03 | +.25 | +.28[b] | +.64[b] | +.20 |
| Escape Latency (sec) | +.12 | +.03 | +.21 | +.40 | +.57[a] |
| Longest Run of Avoidance Responses | +.12 | −7.25 | −8.12 | −23.12 | −39.87[b] |
| Loss of Escape Response (% of total trials) | 0 | 0 | 0 | 0 | 0 |

[a] $p \leq .05$ t test, two tailed
[b] $p \leq .01$ t test, two tailed

Table III

Mean Values Under Control and Drug Conditions for Naive Rats
Dose — 5 minutes Post Injection

| Measure | Control | 2.25 mg/kg | 4.5 mg/kg | 9.0 mg/kg |
|---|---|---|---|---|
| Total Avoidance Responses | 30.83 | 16.17[b] | 20.25[a] | 13.00[b] |
| Avoidance Responses Trials 1–50 | 7.58 | 2.92[a] | 3.08[b] | 2.25[b] |
| Avoidance Responses Trials 51–100 | 23.25 | 13.25[b] | 17.17 | 10.75[b] |
| Intertrial Interval Responses | 25.42 | 23.25 | 19.33 | 16.33[a] |
| Escape Latency (sec) | 1.29 | 1.26 | 1.28 | 1.30 |

[a] $p \leq .05$ t test, two tailed.
[b] $P < .01$ t test, two tailed.

Table IV

Mean Difference Between Control and Each Drug Condition for Trained Rats. Positive Numbers Indicate the Drug Score was Higher; Negative Numbers Indicate the Drug Score was Lower Than Control.

| Measure | .035 mg/kg | .07 mg/kg | Dose — 5 minutes Post Injection .14 mg/kg | .28 mg/kg | .56 mg/kg | 1.12 mg/kg |
|---|---|---|---|---|---|---|
| Total Avoidance Responses | −1.875 | −6.375[a] | −5.143[b] | −23.250[a] | −58.143[b] | −75.571[b] |
| Avoidance Responses Trials 1–50 | −1.00 | −3.500[a] | −5.000[b] | −18.375[b] | −29.571[b] | −39.143[b] |
| Avoidance Responses Trials 51–100 | −.875 | −2.875[b] | −.143 | −4.875 | −21.429[b] | −36.429[b] |
| Avoidance Latency (sec) | .154 | .083 | .151 | .526[b] | .727 b | .862 |
| Escape Latency (sec) | −.079 | .066 | .050 | .394 | .191[b] | .119 |
| Longest Run of Avoidance Responses | 1.125 | −17.375[a] | −7.571 | −17.500[a] | −36.571[b] | −36.286[b] |
| Loss of Escape Response (% of Total Trials) | 0 | 0 | 0 | 1.00 | 0 | 0 |

[a] $P \leq .05$ t test, two tailed.
[b] $P \leq .01$ t test, two tailed.

What is claimed is:

1. A method for tranquilizing mammals without general depression comprising administering to a mammal in need of tranquilization an effective amount of a compound of the formula

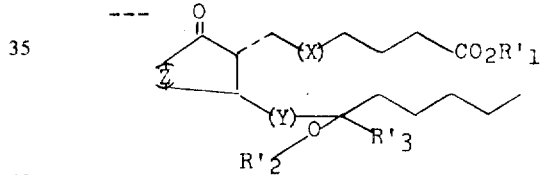

wherein $R_1$ and $R_3$ represent hydrogen or lower alkyl containing 1–7 carbon atoms, $R_2$ represents hydrogen or alkanoyl containing 1–6 carbons, X represents ethyl-ene or cis vinylene, Y represents trans vinylene or ethynylene, and Z represents cis vinylene, or hydroxy- or (lower alkyl)-substituted ethylene in which the methylene portion is adjacent to the carbonyl of the cyclopentane ring in the formula.

2. As in claim 1, a method for tranquilizing mammals without general depression comprising administering to a mammal in need of tranquilization an effective amount of a compound selected from the group consisting of $PGA_2$, 15(S)-acetoxy-9-oxo-5-cis-10,13-trans-prostatrienoic acid, methyl 15(S)-11β,15-dihydroxy-20-methyl-9-oxoprost-13-trans-enoate, 3(RS)2-(3-hydroxy-1-heptynyl)-5-oxocyclopent-1-eneheptanoic acid, 2-(3-hydroxy-1-octynyl)-5-oxocyclopent-1-eneoctanoic acid, methyl (3R)-hydroxy-2α-(3(S)-hydroxy-3R-methyl-1-octynyl)-5-oxocyclopentane-1β-heptanoate, 2-((3RS)-3-hydroxy-1- nonynyl)-3-hydroxy-5-oxocyclopent-1-eneheptanoic acid, and 15(S)-hydroxy-11-methyl-9-oxoprosta-5-cis-13-trans-dienoic acid.

3. As in claim 1, a method for tranquilizing mammals without general depression comprising administering to a mammal in need of tranquilization an effective amount of a compound selected from the group consisting of $PGA_2$ and 15(S)-acetoxy-9-oxo-5-cis-10,13-trans-prostatrienoic acid, and methyl 15(S)-11β,15-dihydroxy-20-methyl-9-oxoprost-13-trans-enoate.

4. As in claim 1, a method for tranquilizing mammals without general depression comprising administering to a mammal in need of tranquilization an effective amount of methyl 15(S)-11β,15-dihydroxy-20-methyl-9-oxoprost-13-trans-enoate.

* * * * *

UNITED STATES PATENT OFFICE
CERTIFICATE OF CORRECTION

PATENT NO. : 3,931,411
DATED : Jan. 6, 1976
INVENTOR(S) : Walter Joseph Potts

It is certified that error appears in the above-identified patent and that said Letters Patent are hereby corrected as shown below:

Column 3, line 13, "by" should read -- to --.

Column 7, line 46, "9oxo" should read -- 9-oxo --.

Column 1, line 31, Formulae III, IV, and V were omitted -- please add after formula II the following:

--

III 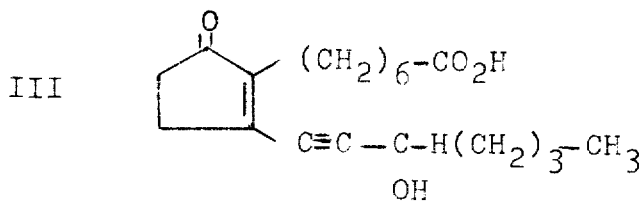

IV 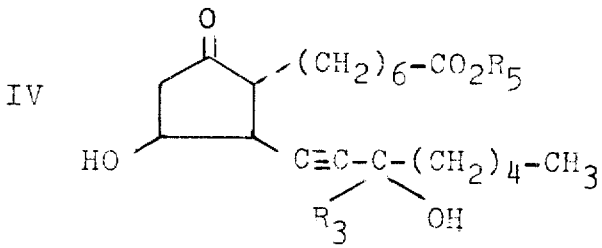

V 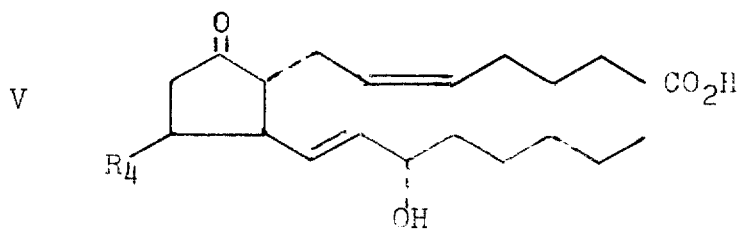

--.

Signed and Sealed this twenty-seventh Day of April 1976

[SEAL]

Attest:

RUTH C. MASON
Attesting Officer

C. MARSHALL DANN
Commissioner of Patents and Trademarks